United States Patent
Jay

[11] Patent Number: 6,129,675
[45] Date of Patent: Oct. 10, 2000

[54] DEVICE AND METHOD FOR MEASURING PULSUS PARADOXUS

[76] Inventor: Gregory D. Jay, 3 Crossbow Rd., Norfolk, Mass. 02056

[21] Appl. No.: 09/151,910

[22] Filed: Sep. 11, 1998

[51] Int. Cl.[7] ...................................................... A61B 5/02
[52] U.S. Cl. ............................ 600/485; 600/323; 600/529
[58] Field of Search ........................... 600/481, 483–485, 600/490, 493, 495, 500, 502, 504, 508–509, 513, 528–529, 323

[56] References Cited

U.S. PATENT DOCUMENTS

| | | | |
|---|---|---|---|
| 3,513,832 | 5/1970 | Klemm et al. .................................. | 5/2 |
| 3,572,317 | 3/1971 | Wade . | |
| 4,365,636 | 12/1982 | Barker ..................................... | 128/716 |
| 4,580,575 | 4/1986 | Birnbaum et al. ....................... | 128/671 |
| 4,958,638 | 9/1990 | Sharpe et al. ............................ | 128/653 |
| 4,958,640 | 9/1990 | Logan ..................................... | 128/671 |
| 5,094,244 | 3/1992 | Callahan et al. ......................... | 128/677 |
| 5,170,794 | 12/1992 | Reiche .................................... | 128/671 |
| 5,396,893 | 3/1995 | Oberg et al. ............................. | 128/671 |
| 5,490,505 | 2/1996 | Diab et al. ............................... | 128/633 |
| 5,507,291 | 4/1996 | Stirbl et al. ........................... | 128/653.1 |
| 5,682,898 | 11/1997 | Aung et al. .............................. | 128/671 |
| 5,980,463 | 11/1999 | Brockway et al. ...................... | 600/485 |

FOREIGN PATENT DOCUMENTS

| | | |
|---|---|---|
| 91/11956 | 8/1991 | WIPO . |
| 97/11637 | 4/1997 | WIPO . |

OTHER PUBLICATIONS

Steele et al., "Pulsus Paradoxus: An Objective Measure with Severity in Croup", AM J Resp. Crit. Care 156:331–334, 1997.

Wright et al., "Continuous, Nonivnasive Measurement of Pulsus Paradoxus in Patients with Acute Asthma", Arch Pediatr. Adolesc. Ned. 150: 914–918, 1996.

Steele et al., (1995) "Continuous Noninvasive Determination of Pulsus Paradoxus: A Pilot Study", Academic Emergency Medicine 2: 894–900.

Wright et al., (1997) "Evaluation of Pre– and Posttreatment Pulse Oximetry in Acute Childhood Asthma", Academic Emergency Medicine 4: 114–117.

International Search Report for PCT/US/20860.

Frey et al., "Pulse oximetry for assessment of pulsus paradousx: a clinical study in children,"*Intensive Care Med* (1998) 24:242–246.

Chadwick et al., "Continous non–invasive assessment pulsus paradoxus," *The Lancet* (1992), pp. 495–496.

*Primary Examiner*—Cary O'Connor
*Assistant Examiner*—Ryan Carter
*Attorney, Agent, or Firm*—Testa, Hurwitz & Thibeault, LLP

[57] ABSTRACT

A device and method are disclosed for electronically measuring the degree of pulsus paradoxus in a patient from a single patient data source. The single data source may be any device that outputs a waveform indicative of patient pulsatile cardiovascular behavior such as an optical plethysmograph, a pulse oximeter, or a blood pressure monitor. The invention is useful for rapidly assessing the status of a patient in acute respiratory distress for the purpose of objectively determining the severity of their condition.

14 Claims, 6 Drawing Sheets

DEVICE AND METHOD FOR MEASURING PULSUS PARADOXUS

FIELD OF THE INVENTION

The invention relates to a device and method for the diagnosis, prognosis, and monitoring of patients afflicted with a variety of clinical syndromes such as asthma, croup, tension pneumothorax, pericardial tamponade, pulmonary embolus, hypovolemic shock, and sleep apnea. More particularly, the invention relates to a non-invasive device and method for monitoring the presence and degree of pulsus paradoxus using patient data obtained from a single source. The invention is useful for rapidly assessing the status of a patient in acute respiratory distress for the purpose of objectively determining the severity of their condition.

BACKGROUND OF THE INVENTION

The medical term pulsus paradoxus refers to a quantifiable, exaggerated decrease in arterial blood pressure during inspiration. In normal patients, the decrease in arterial blood pressure during inspiration is in the range of about 2–5 mm Hg; whereas, in a patient suffering from certain medical conditions, pulsus paradoxus during inspiration may exceed this range and be on the order of 5–20 mm Hg or higher. Pulsus paradoxus has been noted in a variety of medical conditions including, but not limited to, asthma, croup, tension pneumothorax, pericardial tamponade, pulmonary embolus, hypovolemic shock, and sleep apnea.

The mechanisms of pulsus paradoxus are incompletely understood and may differ from disease process to disease process. In severe acute asthma, for example, large intrathoracic pressure variations are created by air trapping, causing a net increase in intraluminal airway pressure. The increased airway pressure is mechanically translated into increased intrapleural pressure, from a dramatically negative intrapleural pressure level during inspiration, to a positive intrapleural pressure level during expiration. Elevated intrathoracic pressure translates to increased impedance to right ventricular ejection which causes a markedly impaired left ventricular stroke output and concomitant reduction of left ventricular preload. These alterations contribute to paradoxic pulse in asthma and other respiratory and cardiovascular disease states.

Although measurement of pulsus paradoxus is recommended by authoritative medical practice guidelines (Steel et al., Acad Emerg Med 2:894–900 (1995); National Heart Lung and Blood Institute (NHLBI Guidelines for Emergency Department Asthma Management, NIH Publication, 1995), pulsus paradoxus is rarely recorded in clinical practice. Resistance by physicians to the application of pulsus paradoxus for the objective assessment of disease severity, asthma in particular, is largely due to the difficulty in measuring pulsus paradoxus in a rapidly breathing patient by methods known currently.

One conventional method for measuring pulsus paradoxus in a hospital emergency room setting is by the application of a sphygmomanometer, commonly referred to as a blood pressure cuff, that is cyclically inflated/deflated near a patient's systolic blood pressure. The operator determines systolic pressure during inspiration and expiration in separate maneuvers. This requires simultaneous observation of respiratory phase and cuff pressure. Typically, multiple operator efforts are required in order to arrive at a systolic pressure during inspiration and expiration. The objective is to determine how much the patient's blood pressure decreases during inspiration by bracketing the decrease in blood pressure within the cyclically varied cuff pressure. This process is ergonomically very difficult to perform and made even more so by the rapidly breathing patient. As a result, the method is inaccurate and interobserver results are excessively variable.

Despite problems inherent in this method of detecting pulsus paradoxus, the advantages of measuring and monitoring pulsus paradoxus are significant. A non-effort dependent, non-invasive measurement that provides immediate insight into how troubled is the act of breathing would be invaluable in the emergency room setting. The National Heart Lung and Blood Institute (NHLBI Guidelines for Emergency Department Asthma Management, NIH Publication, 1995) recognizes the advantages of measuring pulsus paradoxus and has recommended that pulsus paradoxus be measured on all asthmatic patients, despite inherent inaccuracies of the sphygmomanometric technique. Moreover, the NHLBI has advised that any patient with a pulsus paradoxus of 12 mm Hg or greater be hospitalized.

Common measures used currently to assess the severity of asthma are clinical assessment, arterial blood gas analysis, spirometry, and pulse oximetry; however, all are subject to certain shortcomings. Clinical assessment scores, for example, exhibit marked interobserver variability and have been incompletely validated. Arterial blood gas analysis is an invasive and painful technique and is often complicated by therapeutic administration of $O_2$ and β-adrenergic drugs and is therefore unreliable as an indicator of asthma severity. Tests of forced expiratory flow, as in spirometry, are effort dependent, typically cannot be used with children, and may actually exacerbate the underlying disease process.

Many experts are stymied to explain the rising mortality of asthmatic patients in view of the improving quality of acute pharmacological management of asthma and the enhanced sophistication of emergency physicians, as well as pre-hospital care systems. One explanation lies in the observation that there has been little change in how the asthmatic patient is evaluated acutely. A recent development in assessing acute asthma has been the use of pulse oximetry ($SPO_2$) which measures the degree of oxygen saturation of hemoglobin non-invasively and empirically. Despite the ubiquitous availability of oximetry, P-adrenergic drugs, used widely, may result in ventilation-perfusion shunts leading to a fall in $SPO_2$ even though the patient is improving. It would appear that, $SPO_2$, alone is an insensitive indicator of impending or continued respiratory distress.

A commonly used measure of asthmatic severity is peak flow rate (PFR) measurement. Despite widespread and long-standing use, PFR has been found to correlate poorly with asthma severity. This is not unexpected, given that a patient with a breathing impediment is asked to exhale as rapidly as possible against a fixed respiratory resistance. The best of three PFR values is typically used as a clinical measure. Subsequent measurements are taken to assess continually the severity of an asthmatic "attack" and how well the attack is resolving. Sudden death attributable to the necessary exertion required of an acutely asthmatic patient has been reported. Further, neither $SPO_2$ nor PFR techniques can accurately determine whether a child needs to be admitted for asthma because PFR cannot be used in children less than 5 years of age and both measures have proven to be insensitive. $SPO_2$ and PFR techniques correlate imperfectly with asthma severity.

New methods and devices are needed to reliably measure pulsus paradoxus. Surmounting the difficulties in measuring pulsus paradoxus will assist physicians in treating patients with pulsus paradoxus-associated diseases by quickly identifying those who are in more severe distress than apparent, from those who are rapidly responding to standard therapies. For example, in a prospective clinical study of 85 asthmatic children, it was reported that a pulsus paradoxus measurement of 11 mm Hg differentiated those children who needed hospitalization from those who did not (Wright et al., Arch. Ped. Adol. Med. 150:914–918 (1996)). An initial measurement of pulsus paradoxus may accurately determine the need for hospital admission among patients.

SUMMARY OF THE INVENTION

What is needed for emergency rooms and respiratory therapy units is a non-invasive, inexpensive, reliable, objective device and method for measuring pulsus paradoxus that demonstrates good interobserver consistency for evaluation of patients in acute respiratory distress and for evaluation of the response of patients to therapy. The present invention addresses these needs by employing oximetry and/or plethysmograph technology in combination with a digital signal processing capability to determine the degree of pulsus paradoxus. Digital signal processing also provides the capability to determine respiratory and pulse rate from the same plethysmographic waveform used to measure the degree of pulsus paradoxus.

It is a general object of this invention to provide a device and method for assessment of the severity of disease in patients with respiratory disease. It is a further object of this invention to provide a reliable, reproducible, and objective method and device for measuring pulsus paradoxus in patients for the assessing and monitoring of patients with respiratory disease, in particular, patients suffering from asthma.

According to one method of the invention, data in electronic form indicative of patient cardiovascular pulsatile behavior is obtained. Data indicative of respiration, and data indicative of pulse is extracted from the patient data indicative of cardiovascular pulsatile behavior using signal processing techniques. The pulse data and the respiration data are used to measure the degree of pulsus paradoxus. The pulsatile cardiovascular behavior data obtained from a patient may be obtained advantageously from a single source. The source may be, but is not limited to, any of the following, including, a pulse oximeter, an optical plethysmograph, a non-invasive or an invasive blood pressure monitor, a thoracic impedance plethysmograph, or any device that outputs a waveform corresponding to a patient's pulsatile volume.

The respiration data extracting step and the pulse data extracting step may include the steps of determining a frequency content of the pulsatile cardiovascular behavior data to obtain a first frequency component related to respiration and a second frequency component related to pulse. The first frequency component and second frequency components are determined by waveform analysis to extract distinct frequencies from the complex cardiovascular pulsatile behavior waveform. The first frequency component and the second frequency component may be used to generate data indicative of the presence of pulsus paradoxus. The frequency components may be extracted using real-time Fourier analysis of the digitalized waveform.

Generally, real-time Fourier waveform analysis may be used to generate three sinusoidal signals: a respiratory signal, a pulse signal, and a signal exhibiting a cyclic, periodic decrease in pulse volume that occurs during the height of inspiration, i.e., maximal depth of inspiration. The pulse signal that occurs during the height of inspiration generally possesses the same frequency as the respiratory signal. The periodic decrease in pulse amplitude and volume that occurs during periods of respiratory obstruction is termed the pulsus paradoxus signal.

Other means of waveform analysis may be employed, for example, fast-Fourier waveform analysis, period-amplitude analysis, and real-time Fourier analysis via fast and orthogonal search. Period amplitude analysis (PAA) is performed by an encoded set of instructions that is analytically rigid. A resulting algorithm recognizes a periodically depressed portion of the plethysmographic waveform. This algorithm may typically require a pulse counter or other device to provide an input corresponding to heart rate in order to detect the decreases in plethysmographic amplitude.

Fast-Fourier transform techniques and identification of underlying individual spectral signatures can also be used to generate a signal that is representative of pulsus paradoxus. An unknown factor with this approach relates to the amount of "energy" in the pulsus paradoxus signature, which could preclude its automatic determination in certain situations. The frequency of the pulsus paradoxus signal may be determined by the respiratory rate and the "energy" of the pulsus paradoxus signal may be determined by the amplitude of the pulsus paradoxus. However, by employing a cross-correlation function, this signature, identifiable as the product, will be an exaggerated form of the pulsus paradoxus signal, permitting easier detection. One underlying assumption in fast Fourier transformation is that only frequencies of interest have their spectral energy redistributed among all fast-Fourier coefficients. In fact, frequencies of non-interest may arise since the present Fourier transform is based on a truncated data set. Since the frequencies of interest are generally known in this application, interfering fast-Fourier coefficients are identifiable and therefore excludable.

Alternatively, analytical techniques commonly referred to as "wavelets" or "matching pursuits," which produce the requisite time-bandwidth localization, can be utilized. Specifically, a fast orthogonal search algorithm may be employed. The fast orthogonal search algorithm finds the precise phases and amplitudes to associate with each selected period using the Weiner process, a least-squares minimization technique. This process can be readily visualized when fast-orthogonal search is running. A series of sinusoids are linked and are fit to the data. This resultant signal can then be complexed with the respiratory plethysmographic signal using a cross-correlation function, as described above, to determine the degree of pulsus paradoxus. Respiratory plethysmographic data may be obtained by a priori Fourier transform or (if needed) by an external strain gauge.

The extracted pulse signal may be passed through a frequency counter to quantify and display pulse rate. A signal generator driven by the processed plethysmographic waveform may be used to generate a "clean" or "normalized" pulse signal which can be used in the signal processing schemas.

In order to generate data indicative of pulsus paradoxus, the first frequency component is cross-correlated with the second frequency component. The output of a complex multiplier acting on the processed plethysmographic waveform and the respiratory signal may be passed through a second Fourier transformation to cross-correlate the inputs in order to generate the pulsus paradoxus signal. This allows for identification of decreasing pulse amplitude with inspiration and also, in effect, exaggerates the degree of pulsus paradoxus making pulsus paradoxus more easy to detect. The degree of pulsus paradoxus may be determined by comparing the signal indicative of pulsus paradoxus with the normalized pulse data in a signal comparator. The output of the comparator may be passed through a digital to analog converter to permit scaling of the degree of pulsus paradoxus and measuring of its amplitude by a peak detector. A patient without pulsus paradoxus will generate a cross-correlated signal with little or no amplitude that is compatible with a physiological pulsus during maximal unobstructed inspiration in the normal patient; whereas, a patient with pulsus paradoxus will generate a high amplitude signal indicative of a measurable degree of respiratory obstruction.

In an alternative embodiment, a complex multiplier and second Fourier transformation may be used to cross-correlate between a normalized pulse signal and pulsus paradoxus signal. This allows for the identification of decreasing pulse amplitude with inspiration. The cross-correlated signal $Rxy = \Sigma$ (normalized pulse signal)(pulsus paradoxus signal)

permits the digital identification of the inspiratory phase of a patient's pulse containing pulsus paradoxus as that period when a signal is present.

The magnitude of the cross-correlated signal may be displayed visually, for example, on a counter, meter, light bar, etc., audibly using pitch or intensity, or by any other suitable method and apparatus.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION

Figure 1:
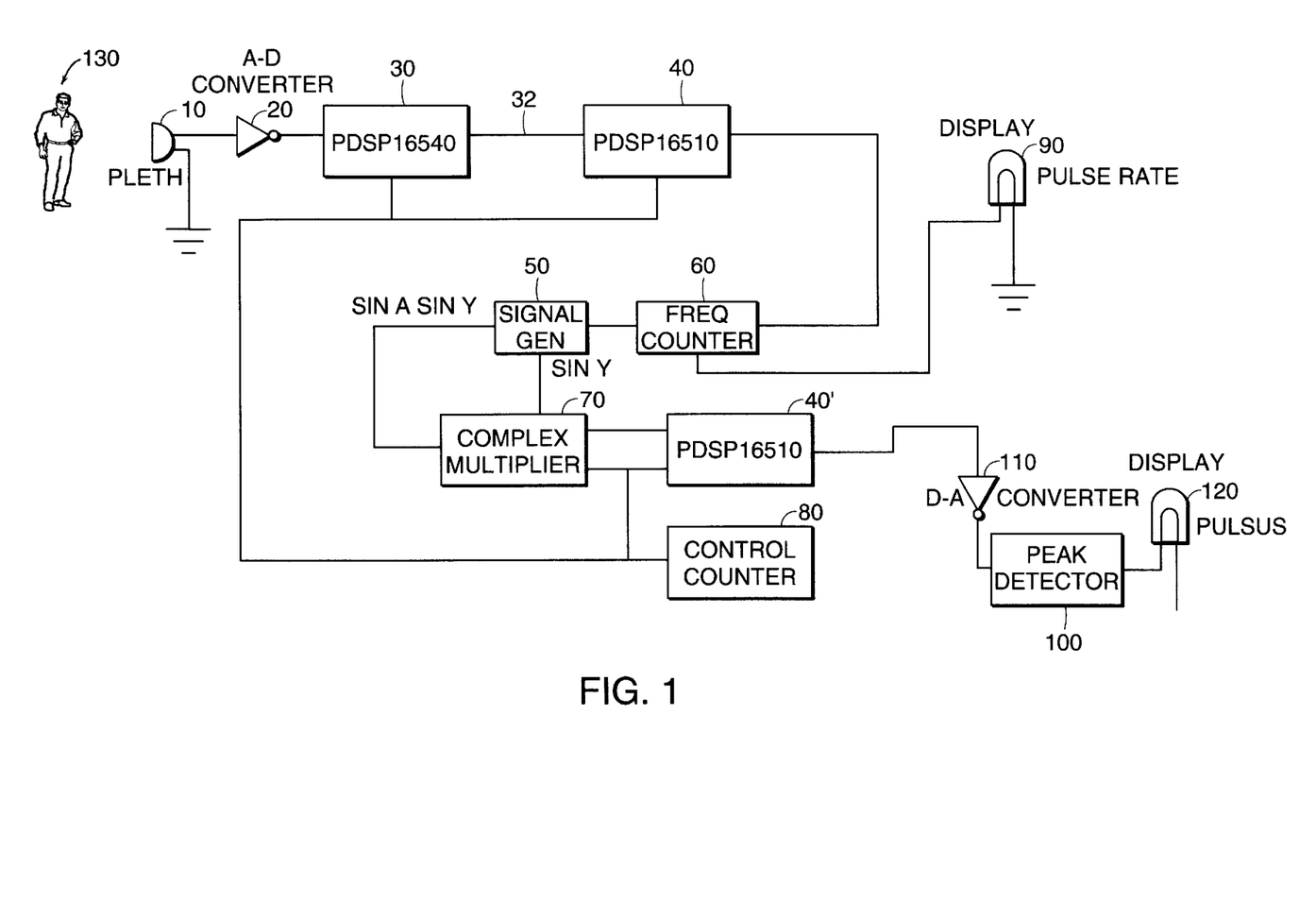
FIG. 1 is one embodiment of a signal processing schematic for measuring the degree of pulsus paradoxus.

FIG. 1 depicts a signal processing schematic of one embodiment of the invention for measuring pulsus paradoxus in a patient. As shown here, analog plethysmographic waveform data from a patient 130 is acquired by a dedicated optical plethysmograph 10, a pulse oximeter, or other similar device. Suitable plethysmographs 10, for example, include TSD100B Optical Plethysmograph (BioPac Systems, Inc., Santa Barbara, Calif.). Suitable oximeters, for example, include Biox 3700 and 3740 (Ohmeda Inc., Madison, Wis.), N-100 (Nellcor, Inc., Pleasanton, Calif.), and N-200 (Nellcor, Inc., Pleasanton, Calif.). The waveform is then digitized by a suitable analog-to-digital converter 20, such as an AD7861 available from Analog Devices located in Norwood, Mass.

Digitized pulsatile waveform information 32 is collected within a PDSP (Plessey Digital Signal Processor) 16450 bucket buffer 30 available from Mitel Corporation located in Caldicot, U.K. The buffer 30, as configured in the schematic, processes real data only. Imaginary input pins are forced to zero level which permits two simultaneous real transforms instead of a single complex transform. This dual transform technique is used to increase the maximum permissible sampling rate to enable 1,024 point transforms to be accomplished in real time.

Output from buffer 30 is projected onto a PDSP 16510 fast Fourier transform (FFT) processor 40 available from Mitel Corporation located in Caldicot, U. K. There are two signals of interest in the FFT output: a) the original pulsatile wave form of patient's pulse without respiratory variation and without pulsus paradoxus (Sin Y) and b) a signal with a frequency corresponding to the patient's heart rate, with a superimposed sinusoidal signal (Sin A Sin Y).

The Sin A Sin Y signal representative of the patient's heart rate is connected to a frequency counter 60 (TCIIO from Yokogawa Inc. Japan), the output of which drives an LED display system 90 to indicate pulse rate.

The pulse signal driving the frequency counter 60 is also connected to a signal generator 50 whose purpose is to generate a clean sinusoidal signal Sin Y that is representative of the transformed Fourier pulse rate (Sin A Sin Y).

The transformed pulse signal (Sin A Sin Y) is complexed with the Fourier transformed pulse rate (Sin Y) in a complex multiplier 70. Both signals, (Sin A Sin Y) and (Sin Y), are presented to a second, stand alone PDSP 16510 FFT processor shown at 40' which performs a cross-correlation function. The cross-correlation function may be represented as:

$Rxy = \Sigma x(n)y(n-m)$.

The product to the right of the sigma is also called the inner-product, where m is the lag variable between the two complexed signals. The cross-correlation function identifies the degree of correlation between pathological and normalized pulsatile signals during inspiration. This is also referred to as pulsus paradoxus and is therefore a capturable phenomenon by effectively multiplying the pathological and normal pulse signals. In effect, the cross-correlation product or inner-product is a sinusoidal signal which contains sinusoidally decreasing amplitude with inspiration as computed by the second FFT processor 40'.

The output of the second FFT processor 40' is presented to a digital to analog converter 110 to convert the digital output to an analog signal. The analog signal passes through a peak detector 100, which monitors the output of the digital to analog converter 110, measures the height of the episodic wave form, and displays a pulsus paradoxus magnitude in numerical or other form on a suitable display 120.

The pulsimeter or plethysmograph spectral filter described in FIG. 1 may be dubbed the PPOx. A readily accessible analog plethysmographic signal may be found on the output of most presently available pulse oximeters. Regardless of the source of the plethysmographic waveform, it is possible by digital signal processing to identify the pulse rate and the underlying respiratory rate within the plethysmographic signal. In pathological situations, such as tension pneumothorax, pericardial tamponade, and severe asthma, both the normalized and pathological pulse signals, when examined by a second digital signal processing technique, permit the identification and the measurement of pulsus paradoxus amplitude and therefore the degree of pulsus paradoxus.

Examples of input and processed waveforms that may be acquired from the above signal processing schema from an untreated patient with asthma and the same patient treated for asthma are illustrated in FIG. 2A–E.

Figure 2A:
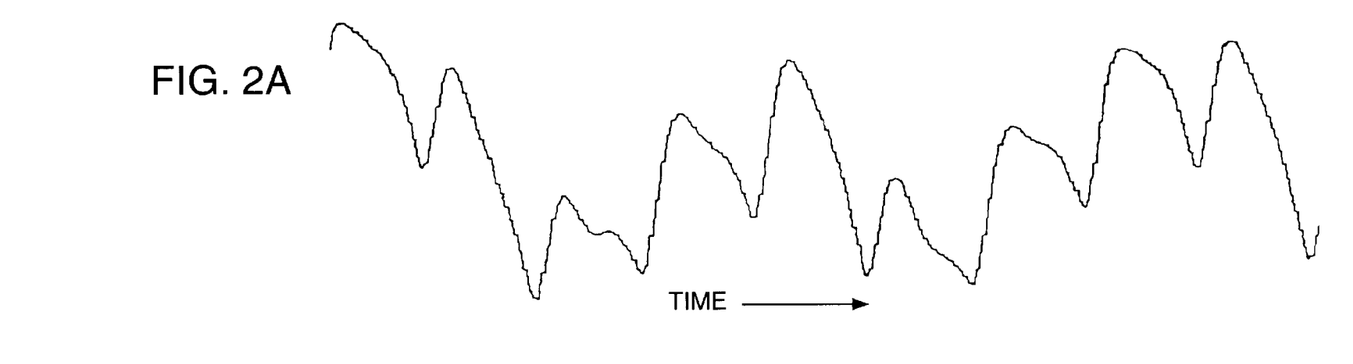
FIG. 2A is a schematic oximetric plethysmographic waveform from an untreated patient experiencing acute asthma.

Illustrated in FIG. 2A is the time domain oximetric plethysmographic waveform (Sin A Sin Y) from an untreated patient with acute asthma, where Sin A is a superimposed sinusoidal signal that has an exaggerated respiratory variation. The exaggerated respiratory variation, as illustrated in this waveform, is an indication of the degree of pulsus paradoxus.

Figure 2B:
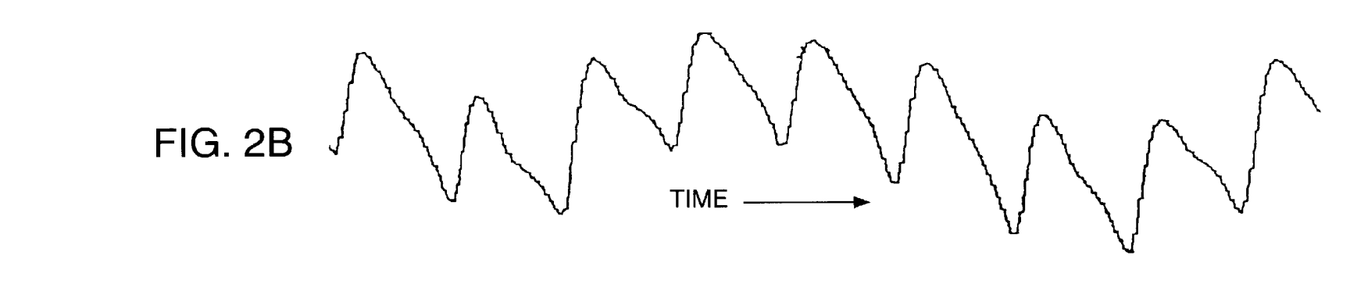
FIG. 2B is a schematic oximetric plethysmographic waveform from a patient experiencing acute asthma and effectively treated with inhaled β-agonist therapy via a nebulizer.

FIG. 2B illustrates a time domain oximetric plethysmographic waveform (Sin A Sin Y) acquired from a patient with asthma following effective treatment with inhaled β-agonist therapy via a nebulizer. Note the diminished peak-to-peak respiratory variation in the waveform of FIG. 2B acquired from a patient effectively treated for asthma, compared to the exaggerated respiratory variation illustrated in the waveform in FIG. 2A acquired from the untreated asthma patient.

Figure 2C:
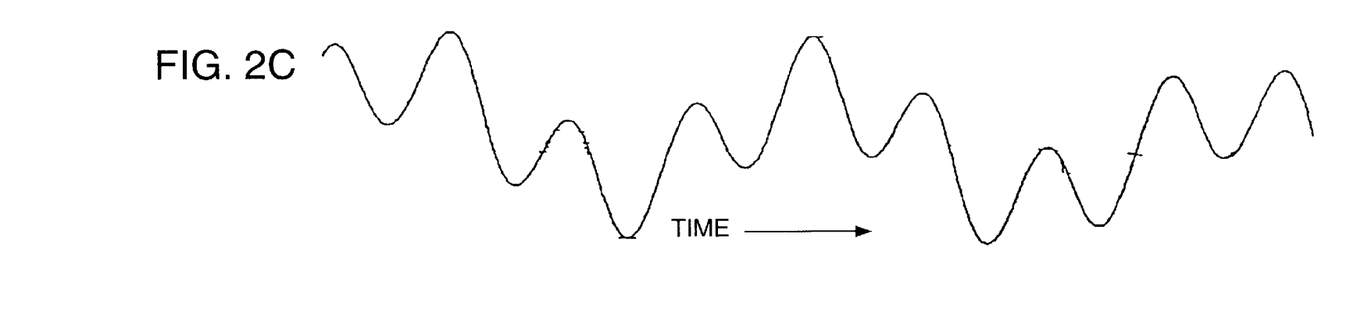
FIG. 2C is a schematic generated waveform which is a normalized replica of an oximetric plethysmographic waveform without pulsus paradoxus containing normal, expected respiratory variation.

FIG. 2C illustrates a transformed Fourier pulse rate time domain signal (Sin Y) generated by the signal processing circuit, which is a normalized replica of the oximetric plethysmographic waveform without pulsus paradoxus. This normalized signal contains the normal and expected amount of respiratory variation. This signal is suitable for digital signal processing.

Figure 2D:
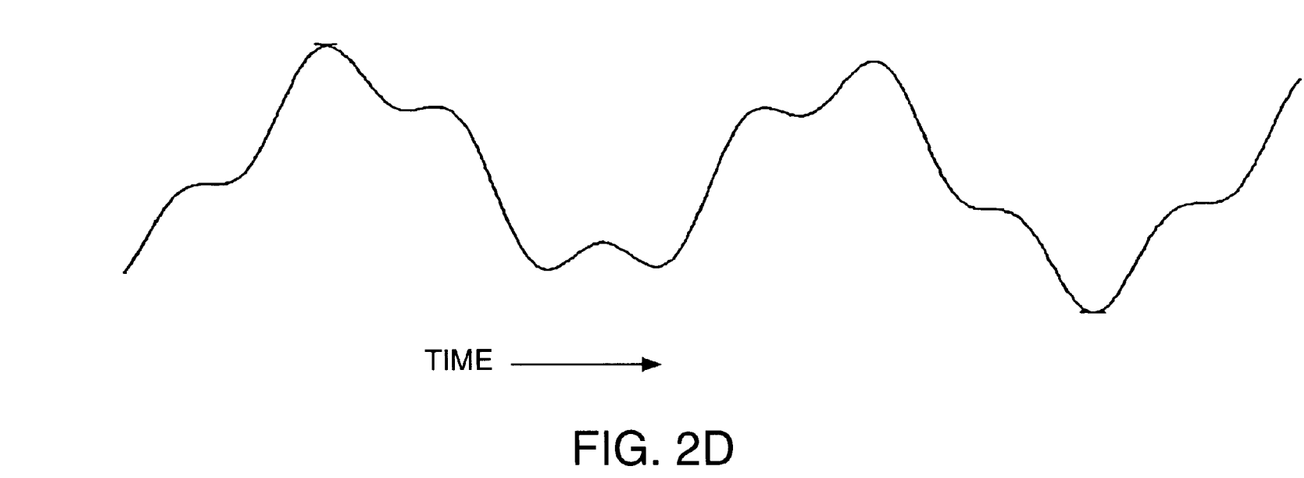
FIG. 2D is a waveform signal from an untreated patient with asthma showing the results of cross-correlation between the waveforms shown in FIG. 2A and FIG. 2C.

FIG. 2D is a time domain waveform generated from the result of cross-correlating the waveforms illustrated in FIG. 2A and FIG. 2C, that is, the oximetric plethysmographic waveform (Sin A Sin Y) from a patient experiencing severe asthma and the normalized pulse rate signal (Sin Y), respectively.

Figure 2E:
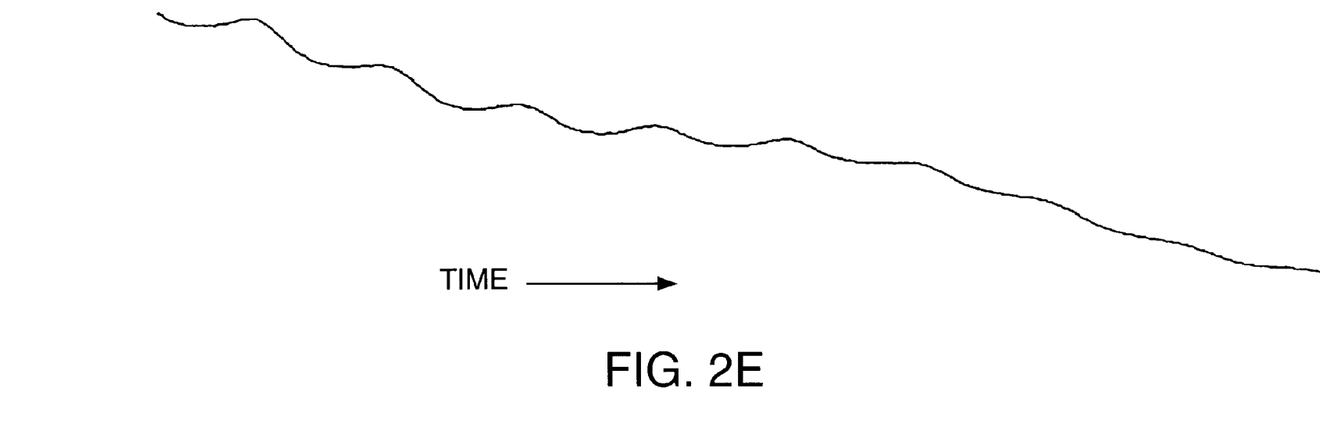
FIG. 2E is a waveform signal from a treated patient with asthma showing the results of cross-correlation between the waveforms shown in FIG. 2B and FIG. 2C.

Illustrated in FIG. 2E is a time domain waveform generated from the result of cross-correlating the waveforms illustrated in FIG. 2B and FIG. 2C, that is the oximetric plethysmographic waveform (Sin A Sin Y) from a patient treated effectively for asthma and the normalized pulse rate signal (Sin Y), respectively.

The digital signals of FIG. 2D and FIG. 2E may be measured directly or converted to analog signals and then measured by a peak detector. The resulting measurement may be displayed as the degree of pulsus paradoxus. Note that the signal from an effectively treated patient illustrated in FIG. 2E is minimal, showing high mathematical cross-correlation between the oximetric plethysmographic waveform (Sin A Sin Y) and the normalized pulse rate signal (Sin Y). By contrast, the cross-correlated signal from the untreated patient reveals relatively high amplitudes (FIG. 2D), indicative of a low mathematical cross-correlation and, accordingly, a large degree of pulsus paradoxus.

Figure 3:
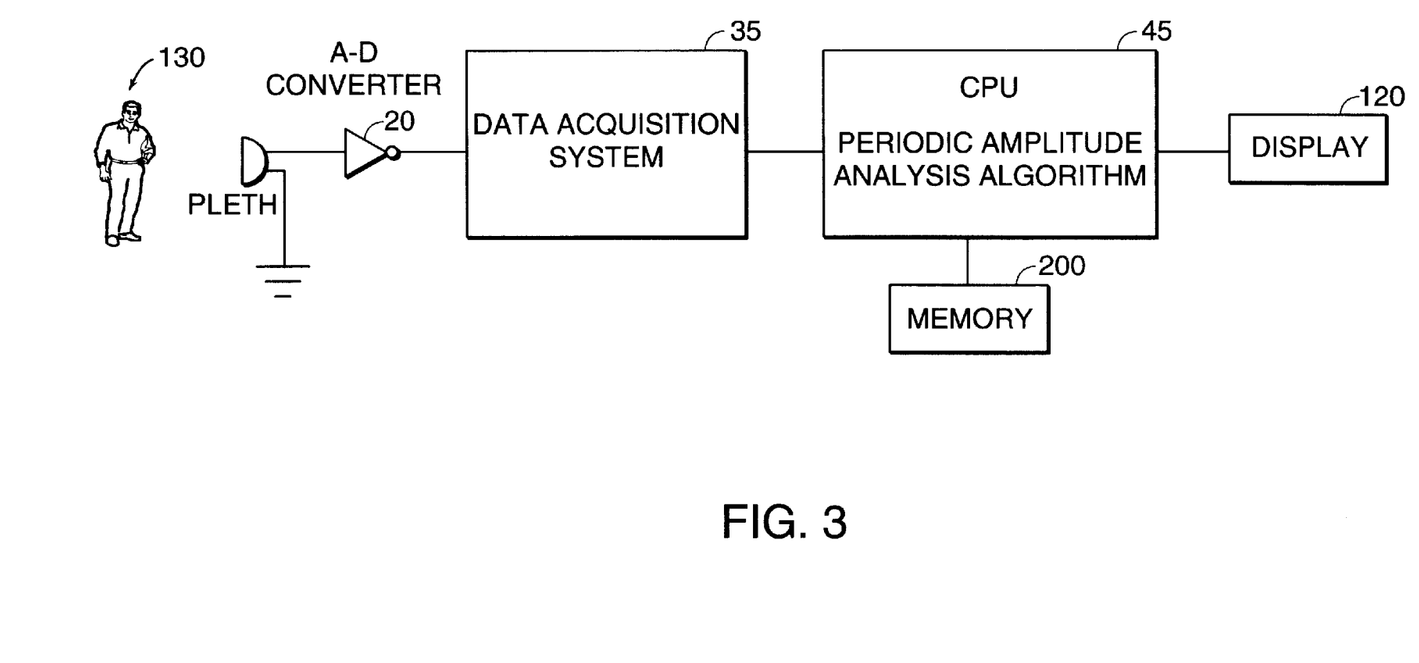
FIG. 3 is another embodiment of a signal processing schematic, including period amplitude analysis, for measuring the degree of pulsus paradoxus.

A second embodiment of the invention using period-amplitude analysis is illustrated in FIG. 3. Unlike previous embodiments, pulsus paradoxus can also be measured and monitored by employing algorithms using period amplitude analysis. These methodologies use a microcomputer (CPU) 45 receiving data from a data acquisition system 35. The data acquisition system 35 collects a predetermined sample of the plethysmographic waveform after digitization by the analog to digital converter 20. Suitable data acquisition systems 35 include Labview (National Instruments, Austin, Tex.) and AcqKnowledge (BioPac Systems, Inc., Santa Barbara, Calif.). The CPU 45 analyzes the waveform and measures the degree of pulsus paradoxus. In the case of period amplitude analysis, the algorithm programs the CPU 45 to identify periodic decreases in plethysmographic amplitude. These decreases are compared to a pre-programmed library 200 of pathologic and normal plethysmographic waveforms where the amount of pulsus paradoxus in mmHg is known for each.

Figure 4:
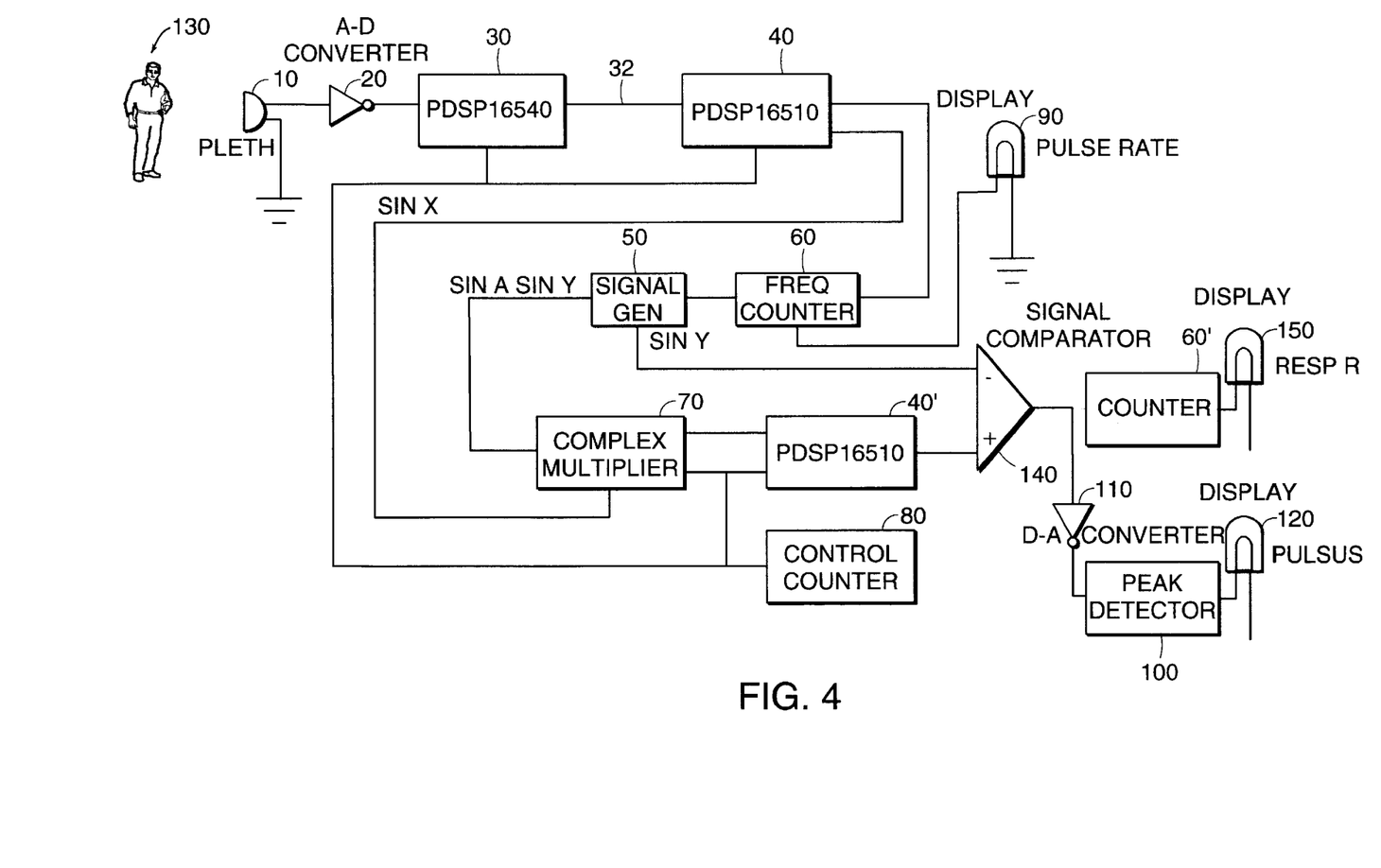
FIG. 4 is yet another embodiment of a signal processing schematic for measuring pulsus paradoxus incorporating the respiratory signal in the signal processing schema which includes two Fourier transforms.

A third embodiment incorporating the respiratory signal in the signal processing schema which includes two Fourier transforms is illustrated in the signal processing schema in FIG. 4. Plethysmographic waveforms are acquired from a patient 130 by a dedicated optical plethysmograph 10 or a pulse oximeter in a manner similar to that described for the embodiments above. The analog waveform is then digitized by a suitable analog-to-digital converter 20 such as a AD7861 (Analog Devices, Norwood, Mass.).

Digitized pulsatile wave form information is collected within a PDSP 16540 bucket buffer 30. The buffer 30, as configured in the schematic, processes real data only. Imaginary input pins are forced to zero level which permits two simultaneous real transforms instead of a single complex transform. This dual transform technique is used to increase the maximum permissible sampling rate to enable 1,024 point transforms to be accomplished in real time.

Output 32 from the buffer 30 is projected onto a PDSP 16510 FFT processor 40. In this embodiment, the two signals of interest in the FFT output are: a) the respiratory component of the original pulsatile wave form, which is present as a signal with a low frequency (Sin X); and b) a signal with a frequency corresponding to the patient's heart rate, with a superimposed sinusoidal signal (Sin A Sin Y).

The respiratory signal (Sin X) is connected to a complex multiplier 70 which is in turn connected to a second PDSP 16510 FFT processor 40'. The signal (Sin A Sin Y) representative of heart rate is connected to a frequency counter 60 and an LED display system 90 to indicate pulse rate. The pulse signal driving the frequency counter 60 is directly connected to a signal generator 50 whose purpose is to generate a clean sinusoidal signal (Sin Y) that is representative of the transformed Fourier pulse rate which is fed to an inverted input of a comparator 140.

The transformed pulse signal (Sin A Sin Y) is complexed with the Fourier transformed respiratory signal (Sin X) in the complex multiplier 70. Both signals, (Sin A Sin Y) and (Sin X), are presented to the stand-alone PDSP 16510 FFT processor 40' which performs a cross-correlation function. The cross-correlation function may be represented as:

$$Rxy = \Sigma x(n) y(n-n).$$

The product to the right of the sigma is also called the inner-product, where m is the lag variable between the two complexed signals. The cross-correlation function identifies the degree of correlation between decreasing pulsatile amplitude with inspiration. This is also referred to as pulsus paradoxus and is therefore a capturable phenomenon by effectively multiplying the respiratory and pulse signals. Low amplitude in the respiratory signal (representative of inspiration) multiplied by the simultaneous decreasing amplitude in the pulse waveform during inspiration is indicative of pulsus paradoxus. By contrast, the low amplitude respiratory signal multiplied by a normal pulse waveform would possess a greater absolute value, indicating no pulsus paradoxus. In effect, the cross-correlation product or inner-product becomes an exaggerated sinusoidal signal which is computed by the second FFT processor 40'.

A signal comparator 140 compares the output from the second FFT processor 40' to the generated transformed pulse rate waveform (Sin Y). The comparator 140 detects when the output of the second FFT processor 40' falls below the lowest amplitude of the clean pulse rate waveform. This is representative of pulsus paradoxus and is subsequently counted by a second frequency counter 60' and displayed by a LED display 150 as respiratory rate.

A peak detector 100 also monitors the output of the signal comparator 140 and measures the height of this episodic waveform. A digital to analog connection 110 may be used prior to passing the signal to a peak detector 100 in order to display a numerical pulsus paradoxus magnitude on a suitable display such as an LED display 120.

Figure 5:
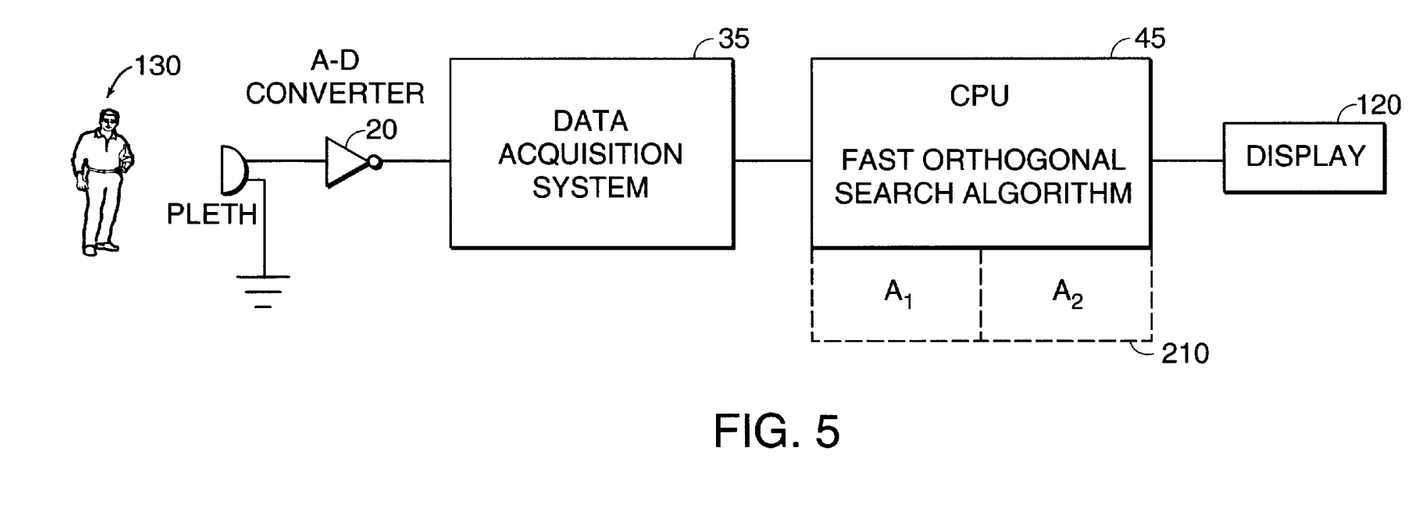
FIG. 5 is still another embodiment of a signal processing schematic for measuring pulsus paradoxus incorporating the respiratory signal in the signal processing schema which includes one Fourier transform and fast orthogonal search.

A fourth embodiment of the invention, illustrated in the signal processing schema in FIG. 5, incorporates the respiratory signal in the signal processing including a single Fourier transformation and fast orthogonal search. Unlike previous embodiments, pulsus paradoxus can also be measured and monitored by employing algorithms 210 using fast orthogonal search. This methodology uses a microcomputer 45 receiving data from a data acquisition system 35. The data acquisition system 35 collects a predetermined sample of the plethysmographic waveform after digitization by the analog to digital converter 20. The algorithm programs the CPU 45 to essentially perform the same set of operations as illustrated in FIG. 1 or FIG. 4. Suitable software capable of performing this analysis, with some modification, is Freq for Windows (CoDebris, Solana Beach, Calif.). A fast orthogonal search algorithm can also identify the respiratory signal and the pathological pulsus paradoxus signal followed by the cross-correlation signal of the two as previously shown in FIG. 4. As illustrated in FIG. 5, this signal is then presented to a separate algorithm (A2) 210 for measurement of pulsus paradoxus and display. Alternatively, the pathological pulsus paradoxus signal is cross-correlated to an undistorted generated signal at the same frequency and amplitude as the patient's plethysmographic waveform (FIG. 1 and FIG. 2). The separate measurement algorithm used above is then employed with a different set of calibration parameters to measure the pulsus paradoxus value.

While certain preferred and exemplary embodiments of the invention have been described, variations, modifications, and other implementations of what is described herein will occur to those of ordinary skill in the art without departing from the spirit and scope of the inventions as claimed. Accordingly, the invention is not to be described by the preceding illustrative description, but instead by the spirit and scope of the following claims.

I claim:

1. A method for measuring pulsus paradoxus in a patient comprising the steps of:

obtaining data indicative of pulsatile cardiovascular behavior from a patient;

extracting data indicative of respiration from the pulsatile cardiovascular behavior data;

extracting data indicative of pulse from the pulsatile cardiovascular behavior data; and using the respiration data and the pulse data to determine pulsus paradoxus.

2. The method of claim 1 wherein the pulsatile cardiovascular behavior data is obtained from a single source.

3. The method of claim 1 wherein the respiration data extracting step and the pulse data extracting step comprise determining a frequency content of the pulsatile cardiovascular behavior data to obtain a first frequency component related to respiration and a second frequency component related to pulse.

4. The method of claim 3 wherein the first frequency component and the second frequency component are used to generate data indicative of presence of pulsus paradoxus.

5. The method of claim 4 wherein the step of generating data indicative of presence of pulsus paradoxus comprises correlating the first frequency component and the second frequency component.

6. The method of claim 5 further comprising the step of determining a degree of pulsus paradoxus by comparing the data indicative of presence of pulsus paradoxus with the pulse data.

7. The method of claim 6 further comprising the step of displaying the degree of pulsus paradoxus.

8. A device for measuring pulsus paradoxus in a patient, the device comprising:

an input for receiving data from a sensor indicative of pulsatile cardiovascular behavior of a patient;

a processor for extracting pulse data and respiration data from the pulsatile cardiovascular behavior data and for generating data indicative of presence of pulsus paradoxus from the pulse data and the respiration data; and an output for outputting at least one of the pulse data, the respiration data, and the data indicative of presence of pulsus paradoxus.

9. The device of claim 8 further comprising a sensor for obtaining the pulsatile cardiovascular behavior data from a single source.

10. The device of claim 8 wherein the processor determines a frequency content of the pulsatile cardiovascular behavior data to obtain a first frequency component related to respiration and a second frequency component related to pulse.

11. The device of claim 10 wherein the processor uses the first frequency component and the second frequency component to generate data indicative of presence of pulsus paradoxus.

12. The device of claim 11 wherein the processor correlates the first frequency component and the second frequency component to generate the data indicative of pulsus paradoxus.

13. The device of claim 12 further comprising a comparator for comparing the pulse data and the data indicative of presence of pulsus paradoxus to determine a degree of pulsus paradoxus.

14. The device of claim 12 further comprising a display for displaying the degree of pulsus paradoxus.

\* \* \* \* \*

UNITED STATES PATENT AND TRADEMARK OFFICE
CERTIFICATE OF CORRECTION

PATENT NO.    : 6,129,675
DATED         : October 10, 2000
INVENTOR(S)   : Jay

It is certified that error appears in the above-identified patent and that said Letters Patent is hereby corrected as shown below:

Title page,
Item [56], OTHER PUBLICATIONS, "Wright et al. (1996)" reference, "Ned." should be deleted and replaced with -- Med. --.
"International Search Report" reference, "PCT/US/20860" should be deleted and replaced with -- PCT/US/99/20860 --.

Column 2,
Line 43, "P-adrenergic", should be deleted and replaced with -- β-adrenergic --.

Column 8,
Line 61, "$Rxy=\Sigma x(n)y(n-n)$" should be deleted and replaced with
-- $Rxy=\Sigma x(n)y(n-m)$ --.

Signed and Sealed this

Sixteenth Day of September, 2003

JAMES E. ROGAN
*Director of the United States Patent and Trademark Office*